United States Patent
Boesveld et al.

(10) Patent No.: US 7,332,638 B2
(45) Date of Patent: Feb. 19, 2008

(54) PROCESS FOR THE PRODUCTION OF TRIPTANE

(75) Inventors: Willem Marco Boesveld, Surrey (GB); Paul Greenough, Bucks (GB)

(73) Assignee: BP Oil International Limited, Middlesex (GB)

( * ) Notice: Subject to any disclaimer, the term of this patent is extended or adjusted under 35 U.S.C. 154(b) by 592 days.

(21) Appl. No.: 10/487,460

(22) PCT Filed: Aug. 15, 2002

(86) PCT No.: PCT/GB02/03752

§ 371 (c)(1),
(2), (4) Date: Feb. 24, 2004

(87) PCT Pub. No.: WO03/020668

PCT Pub. Date: Mar. 13, 2003

(65) Prior Publication Data

US 2004/0249228 A1      Dec. 9, 2004

(30) Foreign Application Priority Data

Aug. 31, 2001 (GB) ............... 0121105.1

(51) Int. Cl.
*C07C 5/13* (2006.01)
(52) U.S. Cl. .................................. 585/737
(58) Field of Classification Search ............ 585/737
See application file for complete search history.

(56) References Cited

U.S. PATENT DOCUMENTS

| | | | |
|---|---|---|---|
| 3,415,736 A | 12/1968 | Ciric | |
| 3,766,286 A | 10/1973 | Olah | |
| 3,878,261 A | 4/1975 | Gardner | |
| 3,972,983 A | 8/1976 | Ciric | |
| 4,714,601 A | 12/1987 | Vaughan | |
| 4,879,103 A | 11/1989 | Vaughan | |
| 4,931,267 A | 6/1990 | Vaughan et al. | |
| 5,116,590 A | 5/1992 | Vaughan et al. | |
| 5,382,730 A * | 1/1995 | Breckenridge et al. | 585/310 |
| 5,763,731 A | 6/1998 | McVicker et al. | |

FOREIGN PATENT DOCUMENTS

| | | |
|---|---|---|
| WO | WO 97/09288 | 3/1997 |
| WO | WO 97/09290 | 3/1997 |
| WO | WO 98/22556 | 5/1998 |
| WO | WO 99/49003 | 9/1999 |
| WO | WO 00/07722 | 2/2000 |
| WO | WO 02/31089 A1 | 4/2002 |

OTHER PUBLICATIONS

Delprato, F. et al; "Synthesis of new silica-rich cubic and hexagonal faujasites using crown-ether-based superamolecules as templates"; *Zeolites*, vol. 10, (1990); pp. 546-552.

Locatelli, F. et al; "Hydrogenolysis of Cyclohexane over $Ir/SiO_2$ Catalyst: A Mechanistic Study of Carbon-Carbon Bond Cleavage on Metallic Surfaces"; *J. Am. Chem. Soc.*, (2001), 123, pp. 1658-1663.

* cited by examiner

*Primary Examiner*—Thuan Dinh Dang
(74) *Attorney, Agent, or Firm*—Nixon & Vanderhye

(57) ABSTRACT

A process for the production of triptane, comprises: providing a hydrocarbon feedstock comprising at least 1 vol % of at least one cyclic hydrocarbon comprising a $C_5$ and/or $C_6$ ring; pre-treating the hydrocarbon feedstock by contacting the hydrocarbon feedstock with a catalyst in the presence of hydrogen, under conditions suitable for selectively opening the ring of the cyclic hydrocarbon; and isomerising the pre-treated feedstock by contacting the pre-treated feedstock with an isomerisation catalyst to produce a triptane-containing product stream.

37 Claims, No Drawings

PROCESS FOR THE PRODUCTION OF TRIPTANE

This application is the U.S. National Phase of International Application PCT/GB02/03752, filed 15 Aug. 2002, which designated the U.S.

The present invention relates to an improved process for the production of triptane.

Triptane, or 2,2,3-trimethylbutane, is a hydrocarbon that is useful in the production of unleaded motor and aviation gasoline (see WO 98/22556 and WO 99/49003). Its highly branched structure makes it particularly useful for enhancing the Motor Octane Number (MON) of fuels.

Various methods for the production of triptane are known. For example, triptane may be produced by reacting a hydrocarbon feedstock, such as naphtha, with an isomerisation catalyst (U.S. Pat. No. 3,766,286 and GB 0024888.0, published as WO 02/31089).

Typically, naphtha feedstocks comprise non-cyclic paraffins, as well as cyclic hydrocarbons such as naphthenes and aromatic compounds. Under the reaction conditions, non-cyclic paraffins in the naphtha feedstock readily isomerise into highly branched hydrocarbons, such as triptane.

It has been found that cyclic compounds are more prone to side-reactions and are hence less likely to be converted into the desired triptane product.

According to the present invention, there is provided a process for the production of triptane, said process comprising:
providing a hydrocarbon feedstock comprising at least 1 vol % of at least one cyclic hydrocarbon comprising a $C_5$ and/or $C_6$ ring;
pre-treating the hydrocarbon feedstock by contacting the hydrocarbon feedstock with a catalyst in the presence of hydrogen, under conditions suitable for selectively opening the ring of the cyclic hydrocarbon; and
isomerising the pre-treated feedstock by contacting the pre-treated feedstock with an isomerisation catalyst to produce a triptane-containing product stream.

The hydrocarbon feedstock may be a hydrocarbon stream boiling in the range of 50 to 110° C. Preferably, the hydrocarbon stream has a boiling range of 60 to 105° C., more preferably 75 to 100° C. The hydrocarbon stream may be an alkylate stream, or preferably, a naphtha stream. More preferably, the naphtha stream is a naphtha stream comprising at least 30 wt %, preferably, at least 50 wt %, for example, 60 to 90 wt % of $C_7$ hydrocarbons.

The hydrocarbon feedstock comprises at least 1 vol % of at least one cyclic hydrocarbon having a $C_5$ and/or $C_6$ ring. Preferably, the hydrocarbon feedstock comprises 2 to 60 vol %, more preferably, 5 to 40 vol %, and more preferably, 10 to 30 vol % of at least one cyclic hydrocarbon having a $C_5$ and/or $C_6$ ring. Cyclic hydrocarbons that may be present include naphthenes and aromatic compounds. Such compounds may be substituted, for example, with alkyl substituents having 1 to 6 carbon atoms, preferably, 1 to 4 carbon atoms, more preferably having 3 or less carbon atoms and most preferably having less than 3 carbon atoms.

Where naphthenes are present, they may be saturated or unsaturated. Preferred naphthenes comprise 6 to 20 carbon atoms, more preferably, 6 to 12 carbon atoms, for example, 6 to 8 carbon atoms. Specific examples include cyclopentane, methyl cyclopentane, dimethyl cyclopentane (e.g. 1,1-dimethylcyclopentane, 1, 2-dimethyl cyclopentane and 1, 3-dimethyl cyclopentane), ethyl cyclopentane, cyclohexane, methyl cyclohexane, dimethyl cyclohexane, ethyl cyclohexane and n-pentyl cyclohexane.

Preferably, the naphthene content of the hydrocarbon feedstock is 0 to 60 wt %, more preferably, 25 to 50 wt %, and most preferably, 30 to 40 wt %. In a most preferred embodiment, the naphtha feedstock comprises 10 to 35 wt %, preferably, 15 to 25 wt % methyl cyclohexane. The naphtha feedstock may also comprise cyclohexane (e.g. 1 to 5 wt %), 1,1-dimethyl cyclopentane (e.g. 1 to 5 wt %) and/or 1, 3-dimethyl cyclopentane (e.g. 2 to 10 wt %).

Where aromatics are present, they may comprise 6 to 20 carbon atoms, preferably, 7 to 12 carbon atoms. Specific examples include benzene, toluene, dimethyl benzene, ethyl benzene and n-butyl benzene. Preferably, the aromatic content of the hydrocarbon feedstock is 0 to 10 wt %, more preferably, 1 to 5 wt %. In a most preferred embodiment, the naphtha feedstock comprises 0 to 5 wt %, preferably, 0 to 2 wt % benzene and/or toluene.

In a preferred embodiment, the feedstock comprises both naphthenes and aromatics.

The remainder of the hydrocarbon feedstock may comprise non-cyclic paraffins. Such paraffins may form 1 to 99 vol % of the overall hydrocarbon feedstock. Preferably, such paraffins form at least 30 vol %, for example, 50 to 80 vol %, more preferably, 60 to 80 vol % of the hydrocarbon feedstock. The non-cyclic paraffins may have 4 to 20 carbon atoms, preferably, 6 to 10 carbon atoms, and more preferably, 6 to 8 carbon atoms. Examples of non-cyclic alkanes that may be present in the feedstock include iso-pentane, 3-methyl pentane, n-hexane, 2, 2-dimethyl pentane, 2, 4-dimethyl pentane, 3, 3-dimethyl pentane, 2, 3-dimethyl pentane, 2-methyl hexane, 3-methyl hexane, 3-ethyl pentane, n-heptane, dimethyl hexane, and methyl heptane.

In a preferred embodiment, the hydrocarbon feedstock is a naphtha stream comprising a major proportion of $C_7$ hydrocarbons, and a minor amount of a $C_5$, $C_6$ and/or $C_8$ hydrocarbon. Examples of $C_5$ hydrocarbons that may be present include iso-pentane. Examples of $C_6$ hydrocarbons that may be present include 3-methyl pentane, n-hexane, cyclohexane and benzene. Examples of $C_7$ hydrocarbons that may be present include, 2, 2-dimethyl pentane, 2, 4-dimethyl pentane, 3, 3-dimethyl pentane, 1, 1-dimethyl cyclopentane, 1, 3-dimethyl cyclopentane, 2, 3-dimethyl pentane, 2-methyl hexane, 3-methyl hexane, 3-ethyl pentane, n-heptane, methyl cyclohexane and toluene. Examples of $C_8$ hydrocarbons that may be present include dimethyl hexane, and methyl heptane. The hydrocarbon feedstock may comprise:
25 to 40 vol % n-heptane;
10 to 28 vol % of a mono-branched $C_7$;
5 to 15 vol % of a di-branched $C_7$;
20 to 40 vol % naphthenes, and
0 to 5 vol % aromatics.

In the pre-treatment step, the hydrocarbon feedstock is contacted with a catalyst in the presence of hydrogen. Under the reaction conditions, at least some of the $C_5$ and/or $C_6$ ring structures present in the hydrocarbon feedstock are selectively opened to form linear or branched aliphatic structures. For example, any methyl cyclohexane present in the hydrocarbon feedstock is preferably converted to 2, 4 dimethyl pentane.

Such ring opening reactions have the effect of reducing the number of ring structures in the hydrocarbon feedstock, whilst preferably, avoiding significant dealkylation of any pendant substituents on the ring. Thus, in preferred embodiments of the invention, there is substantially no fragmentation of the cyclic compound. The selectivity of the ring-forming reaction is preferably at least 10%, preferably, at least 50%, for example, 80 to 99%.

In addition to the ring-opening reaction described above, preferably, addition of hydrogen across unsaturated bonds occurs. This may also be accompanied by rearrangement reactions. For example, any benzene present in the feedstock is preferably hydrogenated under the reaction conditions to form cyclohexane. This cyclic compound may then be "opened" to produce, for example, 2-methyl pentane.

Suitable ring-opening catalysts contain both a metal function and an acidic function. The metal function may be performed by using an effective amount of a Group VIII metal. Suitable Group VIII metals include Fe, Ru, Os, Co, Rh, Ir, Ni, Pd, and mixtures thereof. Of these, Rh, Ir and Ru are preferred. Ir is particularly preferred. The amount of metal employed may range from 0.01 to 10 wt %, preferably, 0.02 to 5 wt %, more preferably, 0.05 to 3 wt % and most preferably, 0.1 to 1 wt %.

The acid function may be provided by a zeolitic material. Such zeolitic materials may be employed to support the metals described above. Preferably, the zeolitic material is of the faujastic type having an Si/M ratio of at least 30, wherein M is at least one element selected from Al, Ga, B, Zn, Re and Cr. Preferably, M is Al, and the Si/Al ratio of the zeolitic material is at least 60. Examples of preferred zeolitic materials are described in U.S. Pat. No. 4,714,601 (ECR-4 materials), U.S. Pat. No. 4,879,103 (ECR-30 materials), U.S. Pat. No. 4,931,267 (ECR-32 materials), U.S. Pat. No. 5,116,590 (ECR-35 materials), U.S. Pat. No. 3,415,736 (ZSM-3 materials), and U.S. Pat. No. 3,972,983 (ZSM-20 materials). Analogues of such zeolites may also be employed, such as EMC-1 and EMC-2 (Delpratop et al, zeolites, 10, p 546-552 (1990)). Other examples of suitable zeolitic materials include mordenite, Y, beta, MCMs, clay, montmorrelite materials, and ITQ-6 materials. An ITQ-6 material is an oxide, which in its calcined form has an X-ray diffraction pattern that includes the figures in the table below. The material has a microporous surface area of ITQ-6 (as determined by the $N_2$ adsorption desorption method) of at least 400 $m^2/g$, and an external surface area (also determined by the $N_2$ adsorption desorption method) of at least 350 $m^2/g$. ITQ-6 materials are described in detail in PCT/GB99/02567, which is incorporated herein by reference.

TABLE

| d (Angstroms) | I/Io * 100 |
|---|---|
| 9.50 +/− 0.19 | f |
| 7.10 +/− 0.14 | f |
| 6.62 +/− 0.13 | m |
| 5.68 +/− 0.11 | d |
| 3.97 +/− 0.08 | f |
| 3.73 +/− 0.07 | f |
| 3.53 +/− 0.07 | mf |
| 3.16 +/− 0.06 | m |

In this table the letters stand for the following:
f=strong 40-60% relative intensity
mf=very strong 60-100% relative intensity
m=medium 20-40% relative intensity
d=weak 0-20% relative intensity The pre-treatment step is preferably carried out at 150 to 400° C., more preferably, at 225 to 350° C. Pressures of 0 to 208.6 barg (0 to 3000 psig), preferably, 6.9 to 151.7 barg (100 to 2200 psig), and more preferably, 6.9 to 103.4 barg (100 to 1500 psig) may be employed. The hydrocarbon feedstock may be passed over the catalyst at a liquid hourly space velocity of 0.1 to 10, preferably, 0.5 to 5 LHSV ($h^{-1}$).

In a preferred embodiment, the hydrogen treat gas rate is maintained at 60 to 2000 $m^3$ of hydrogen per $m^3$ of hydrocarbon reactant, preferably, 100 to 600 $m^3$ of hydrogen per $m^3$ of hydrocarbon reactant.

Ring opening reactions are described in general in WO 97/09288, WO 97/09290 and U.S. Pat. No. 5,763,731.

Once pre-treated, the hydrocarbon feedstock is contacted with an isomerisation catalyst to produce a triptane-containing product stream.

The isomerisation catalyst employed is preferably a superacid. Suitable superacids include Lewis acid of the formula $MX_n$, where M is an element selected from Group 13, 14, 15 and 16 of the Periodic Table, X is a halogen, and n is an integer of 3 to 6. Preferably, M is selected from Groups 13 and 15 of the Periodic Table. More preferably, M is Sb. X may be F, Cl, Br or I, and preferably, is F or Cl. In preferred embodiments of the invention, M is employed in its highest valency state with the selected halogen. Thus, in a most preferred embodiment of the invention, the Lewis acid is $SbF_5$.

Preferably, the Lewis acid is employed in combination with a Bronsted acid for example HX (wherein X is a halogen), fluorosulfuric acid, trifluoromethanesulfonic acid and/or trifluoroacetic acid. Preferred examples of suitable isomerisation catalysts are $HSO_3F$—$SbF_5$ and $SbF_5$—HF. The molar ratio of Bronsted acid to Lewis acid can range from about 20:1 to 1:5. Preferably, a 5:1 to 1:1 molar ratio is employed. The amount of the catalyst employed with reference to the total amount of hydrocarbon used may range from about 0.01 to 100 parts by weight of the catalyst per part by weight of hydrocarbon. Preferably, the amount of catalyst employed is 1 to 10 parts by weight of the catalyst per part by weight of the hydrocarbon.

The catalyst may be used as the neat liquid, as a diluted solution or adsorbed on a solid support. With regard to the diluted catalyst, any diluent may be used that is inert under the reaction conditions. To obtain optimum results, the diluents may be pre-treated to remove catalyst poisons such as water, unsaturated compounds and the like. Typical diluents include sulfuryl chloride fluoride, sulfuryl fluoride, fluorinated hydrocarbons and mixtures thereof. Protic acids including fluorosulfuric acid, sulphuric acid, trifluoromethanesulfonic acid and the like, themselves, can be used as diluents. The diluent:catalyst volume ratio can range from about 50:1 to 1:1 and, preferably, from 10:1 to 2:1.

The catalyst may alternatively be incorporated with a suitable solid carrier or support. Any solid catalyst support may be used that is substantially inert to the catalyst under the reaction conditions. The support may be pre-treated, such as by heating, chemical treatment or coating, to remove substantially all water and/or hydroxylic sites that might be present. Active supports may be rendered inert by coating them with an inert material such as antimony trifluoride or aluminium trifluoride. Suitable solid supports include fluoride-treated or coated resins such as sulfonated cation exchange resins, fluoride-treated acidic chalcides such as alumina and aluminosilicates, and acid-resistant molecular sieves such as a zeolite, e.g. faujasite. The supported catalysts can be prepared in any suitable manner, such as by conventional methods including dry mixing, co-precipitation or impregnation. In one embodiment, the supported catalyst is prepared by impregnating a suitable deactivated support with a metal fluoride such as antimony pentafluoride and then with a Bronsted acid such as fluorosulfuric acid.

When a supported catalyst is employed, the weight ratio of the Lewis acid to the support may range from 1:100 to 1:10 and preferably, from 1:50 to 1:35. The weight ratio of the Bronsted acid to the support may range from 1:100 to 1:10 and, preferably, from 1:50 to 1:35.

The isomerisation reaction may be carried out at −50 to 100° C. Preferably, the reaction temperature is −30 to 25° C., more preferably, −25 to 10° C., even more preferably, −15 to 5° C., most preferably, −10 to 0° C.

The contact time may be 0.01 to 150 hours, preferably, 0.05 to 50 hours, more preferably, 0.08 to 24 hours, yet more preferably, 0.1 to 15 hours, and most preferably, 4 to 6 hours.

Preferably, the triptane selectivity is at least 7%, more preferably, at least 9%. For example, the triptane selectivity may be between 9 and 60% of the initial hydrocarbon feedstock.

Conditions for isomerising hydrocarbon feedstocks are described in general terms in GB 0024888.0 (published as WO 02/31089) and U.S. Pat. No. 3,766,286.

The invention claimed is:

1. A process for the production of triptane, said process comprising:
    providing a hydrocarbon feedstock which is a naphtha stream comprising at least 30 wt % of $C_7$ hydrocarbons and which comprises at least 1 vol % of at least one cyclic hydrocarbon comprising a $C_5$ and/or $C_6$ ring;
    pre-treating the hydrocarbon feedstock by contacting the hydrocarbon feedstock with a catalyst in the presence of hydrogen, under conditions suitable for selectively opening the ring of the cyclic hydrocarbon; and
    isomerising the pre-treated feedstock by contacting the pre-treated feedstock with an isomerisation catalyst to produce a triptane-containing product stream.

2. A process as claimed in claim 1 in which the hydrocarbon feedstock is a hydrocarbon stream boiling in the range of 50 to 110° C.

3. A process as claimed in claim 2 in which the naphtha stream comprises at least 50 wt % of $C_7$ hydrocarbons.

4. A process as claimed in claim 3 in which the naphtha stream comprises 60 to 90 wt % of $C_7$ hydrocarbons.

5. A process as claimed in claim 1 in which the hydrocarbon feedstock comprises 2 to 60 vol % of at least one cyclic hydrocarbon having a $C_5$ and/or $C_6$ ring.

6. A process as claimed in claim 5 in which the at least one cyclic hydrocarbon is selected from the group consisting of naphthenes and aromatic compounds, optionally substituted with alkyl substituents having 1 to 6 carbon atoms.

7. A process as claimed in claim 6 in which independently, the naphthenes comprise 6 to 20 carbon atoms and the aromatic compounds comprise 6 to 20 carbon atoms.

8. A process as claimed in claim 7 in which the at least one cyclic hydrocarbon is selected from the group consisting of cyclopentane, methyl cyclopentane, dimethyl cyclopentanes, ethyl cyclopentane, cyclohexane, methyl cyclohexane, dimethyl cyclohexane, ethyl cyclohexane, n-pentyl cyclohexane, benzene, toluene, dimethyl benzene, ethyl benzene and n-butyl benzene.

9. A process as claimed in claim 5 in which the ring-opening catalyst contains both a metal function and an acidic function.

10. A process as claimed in claim 5 in which the hydrocarbon stream comprises 5 to 40 vol % of at least one cyclic hydrocarbon having a $C_5$ and/or $C_6$ ring.

11. A process as claimed in claim 5 in which the hydrocarbon stream comprises 10 to 30 vol % of at least one cyclic hydrocarbon having a $C_5$ and/or $C_6$ ring.

12. A process as claimed in claim 1 in which the at least one cyclic hydrocarbon is selected from the group consisting of naphthenes and aromatic compounds, optionally substituted with alkyl substituents having 1 to 6 carbon atoms.

13. A process as claimed in claim 12 in which independently, the naphthenes comprise 6 to 20 carbon atoms and the aromatic compounds comprise 6 to 20 carbon atoms.

14. A process as claimed in claim 13 in which the at least one cyclic hydrocarbon is selected from the group consisting of cyclopentane, methyl cyclopentane, dimethyl cyclopentanes, ethyl cyclopentane, cyclohexane, methyl cyclohexane, dimethyl cyclohexane, ethyl cyclohexane, n-pentyl cyclohexane, benzene, toluene, dimethyl benzene, ethyl benzene and n-butyl benzene.

15. A process as claimed in claim 12 in which the ring-opening catalyst contains both a metal function and an acidic function.

16. A process as claimed in claim 1 in which the hydrocarbon feedstock comprises:
    25 to 40 vol % n-heptane;
    10 to 28 vol % of a mono-branched $C_7$;
    5 to 15 vol % of a di-branched $C_7$;
    20 to 40 vol % naphthenes, and
    0 to 5 vol % aromatics.

17. A process as claimed in claim 16 in which the ring-opening catalyst contains both a metal function and an acidic function.

18. A process as claimed in claim 17 in which the metal function is performed by using an effective amount of a Group VIII metal and the acid function is provided by a zeolitic material.

19. A process as claimed in claim 18 in which the isomerisation catalyst is a superacid.

20. A process as claimed in claim 19 in which the superacid is a Lewis acid of the formula $MX_n$, where M is an element selected from the group consisting of Group 13, 14, 15 and 16 of the Periodic Table, X is a halogen, and n is an integer of 3 to 6.

21. A process as claimed in claim 20 in which the Lewis acid is employed in combination with a Bronsted acid.

22. A process as claimed in claim 21 in which the Bronsted acid is HX (wherein X is a halogen), fluorosulfuric acid, trifluoromethanesulfonic acid and/or trifluoroacetic acid.

23. A process as claimed in claim 17 in which the isomerisation catalyst is a superacid.

24. A process as claimed in claim 1 in which the ring-opening catalyst contains both a metal function and an acidic function.

25. A process as claimed in claim 24 in which the metal function is performed by using an effective amount of a Group VIII metal.

26. A process as claimed in claim 25 in which the acid function is provided by a zeolitic material.

27. A process as claimed in claim 26 in which the isomerisation catalyst is a superacid.

28. A process as claimed in claim 27 in which the superacid is a Lewis acid of the formula $MX_n$, where M is an element selected from the group consisting of Group 13, 14, 15 and 16 of the Periodic Table, X is a halogen, and n is an integer of 3 to 6.

29. A process as claimed in claim 28 in which the Lewis acid is employed in combination with a Bronsted acid.

30. A process as claimed in claim 29 in which the Bronsted acid is HX (wherein X is a halogen), fluorosulfuric acid, trifluoromethanesulfonic acid and/or trifluoroacetic acid.

31. A process as claimed in claim 25 in which the metal function is performed using an effective amount of a Group VIII metal selected from the group consisting of Fe, Ru, Os, Co, Rh, Ir, Ni, Pd and mixtures thereof.

32. A process as claimed in claim 24 in which the acid function is provided by a zeolitic material.

33. A process as claimed in claim 24 in which the isomerisation catalyst is a superacid.

34. A process as claimed in claim 1 in which the isomerisation catalyst is a superacid.

35. A process as claimed in claim 34 in which the superacid is a Lewis acid of the formula $MX_n$, where M is an element selected from the group consisting of Group 13, 14, 15 and 16 of the Periodic Table, X is a halogen, and n is an integer of 3 to 6.

36. A process as claimed in claim 35 in which the Lewis acid is employed in combination with a Bronsted acid.

37. A process as claimed in claim 36 in which the Bronsted acid is HX (wherein X is a halogen), fluorosulfuric acid, trifluoromethanesulfonic acid and/or trifluoroacetic acid.

* * * * *